US00PP19725P2

(12) United States Plant Patent
Dekker

(10) Patent No.: US PP19,725 P2
(45) Date of Patent: Feb. 17, 2009

(54) *CHRYSANTHEMUM* PLANT NAMED 'MONA LISA SUNNY'

(50) Latin Name: *Chrysanthemum×morifolium*
Varietal Denomination: Mona Lisa Sunny

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/074,411

(22) Filed: Mar. 3, 2008

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent L Bell
(74) *Attorney, Agent, or Firm*—C. A. Whealy

(57) ABSTRACT

A new and distinct cultivar of *Chrysanthemum* plant named 'Mona Lisa Sunny', characterized by its decorative anemone-type inflorescences with elliptic-shaped, dark yellow-colored ray florets and enlarged disc florets; strong and upright flowering stems; freely flowering habit; early and uniform flowering response; and good postproduction longevity.

1 Drawing Sheet

Botanical designation: *Chrysanthemum×morifolium.*
Cultivar denomination: 'Mona Lisa Sunny'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Mona Lisa Sunny'.

The new *Chrysanthemum* is a naturally-occurring whole plant mutation of the *Chrysanthemum×morifolium* cultivar Mona Lisa Yellow, disclosed in U.S. Plant Pat. No. 18,136. The new *Chrysanthemum* was discovered and selected by the Inventor as a single flowering plant within a population of plants of the cultivar Mona Lisa Yellow on Oct. 4, 2005, in Hensbroek, The Netherlands. The selection of this plant was based on its attractive ray floret color and good inflorescence form.

Asexual reproduction of the new *Chrysanthemum* by terminal cuttings in a controlled environment in a greenhouse in Hensbroek, The Netherlands since Oct. 27, 2005, has shown that the unique features of this new *Chrysanthemum* are stable and reproduced true to type in successive generations.

SUMMARY OF THE INVENTION

Plants of the cultivar Mona Lisa Sunny have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Mona Lisa Sunny'. These characteristics in combination distinguish 'Mona Lisa Sunny' as a new and distinct cultivar of *Chrysanthemum:*

1. Decorative anemone-type inflorescences with elliptic-shaped, dark yellow-colored ray and enlarged disc florets; typically grown as a spray-type.

2. Strong and upright flowering stems.
3. Freely flowering habit.
4. Early and uniform flowering response; plants flower about 50 days after the start of photoinductive treatments.
5. Good postproduction longevity; plants maintain good substance for about 22 days in an interior environment.

Plants of the new *Chrysanthemum* differ from plants of the parent, the cultivar Mona Lisa Yellow, in the following characteristics:

1. Plants of the new *Chrysanthemum* are less vigorous than plants of the cultivar Mona Lisa Yellow.
2. Plants of the new *Chrysanthemum* and the cultivar Mona Lisa Yellow differ in ray floret color as plants of the cultivar Mona Lisa Yellow have light yellow-colored ray florets.

Plants of the new *Chrysanthemum* can be compared to plants of the *Chrysanthemum* cultivar Mona Lisa Cream, disclosed in U.S. Plant Pat. No. 17,812. In side-by-side comparisons conducted in Hensbroek, The Netherlands, plants of the new *Chrysanthemum* differed from plants of the cultivar Mona Lisa Cream in the following characteristics:

1. Plants of the new *Chrysanthemum* were more freely flowering than plants of the cultivar Mona Lisa Cream.
2. Plants of the new *Chrysanthemum* had fewer ray florets per inflorescence than plants of the cultivar Mona Lisa Cream.
3. Plants of the new *Chrysanthemum* and the cultivar Mona Lisa Cream differed in ray floret color as plants of the cultivar Mona Lisa Cream had creamy white-colored ray florets.

BRIEF DESCRIPTION OF THE PHOTOGRAPHS

The accompanying colored photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Mona Lisa Sunny' grown as a natural spray.

The photograph at the bottom of the sheet is a close-up view of a typical flower stem of 'Mona Lisa Sunny'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the winter in Hensbroek, The Netherlands, under commercial practice in a glass-covered greenhouse. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were pinched once and were about nine weeks from planting when the photographs and the description were taken.

Botanical classification: *Chrysanthemum×morifolium* cultivar Mona Lisa Sunny.

Parentage: Naturally-occurring whole plant mutation of the *Chrysanthemum×morifolium* cultivar Mona Lisa Yellow, disclosed in U.S. Plant Pat. No. 18,136.

Propagation:

*Type.*—Terminal vegetative cuttings.

*Time to initiate roots.*—About six to seven days with temperatures about 20° C.

*Time to produce a rooted young plant.*—About 13 to 15 days with temperatures about 20° C.

*Root description.*—Fine; light brown in color.

*Rooting habit.*—Freely branching; moderately dense.

Plant description:

*Appearance.*—Herbaceous decorative anemone-type cut flower that is typically grown as a natural spray.

*Flowering stem description.*—Aspect: Erect. Length: About 75 cm. Spray diameter: About 20 cm to 25 cm. Diameter: About 6 mm to 8 mm. Texture: Pubescent; longitudinally ridged. Color: Close to 146A to 146B.

*Foliage description.*—Arrangement: Alternate; simple. Length: About 7 cm to 14 cm. Width: About 3 cm to 8 cm. Apex: Apiculate. Base: Attenuate. Margin: Palmately lobed; sinuses mostly divergent. Texture, upper and lower surfaces: Pubescent, rough; veins prominent on lower surface. Color: Developing and fully expanded foliage, upper surface: Close to 147A; venation, close to 147B. Developing and fully expanded foliage, lower surface: Close to 147B; venation, close to 146B. Petiole: Length: About 1 mm to 20 mm. Diameter: About 5 mm. Texture, upper and lower surfaces: Pubescent; slightly rough. Color, upper surface: Close to 146B to 146C. Color, lower surface: Close to 146C.

Inflorescence description:

*Appearance.*—Decorative anemone-type inflorescence form with elliptic-shaped ray florets and enlarged disc florets. Inflorescences borne on terminals, arising from leaf axils. Ray and disc florets develop acropetally on a capitulum. Inflorescences moderately fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to two weeks of long day/short night conditions after planting followed by photoinductive short day/long night conditions flower about 50 days later when grown as a natural spray.

*Postproduction longevity.*—In an interior environment, inflorescences and foliage will maintain good color and substance for about 22 days.

*Quantity of inflorescences.*—Freely flowering habit, about 30 to 40 inflorescences per flowering stem develop.

*Inflorescence size.*—Diameter: About 6 cm to 7 cm. Depth (height): About 2 cm. Disc diameter: About 2 cm. Receptacle height: About 4 mm. Receptacle diameter: About 5 mm to 6 mm. Receptacle color: Between 145B and 145C.

*Inflorescence buds.*—Shape: Oblate. Height: About 5 mm to 6 mm. Diameter: About 8 mm to 10 mm. Color: Close to 137C.

*Ray florets.*—Length: About 2 cm to 3.5 cm. Width: About 8 mm to 13 mm. Shape: Elliptic. Aspect: Concave. Apex: Broadly acuminate. Base: Attenuate. Texture: Smooth, glabrous; satiny. Number of ray florets per inflorescence: About 45 arranged in about three whorls. Color: When opening, upper surface: Close to 3A. When opening, lower surface: Close to 3B. Fully opened, upper surface: Close to 4A. Fully opened, lower surface: Close to 5D.

*Disc florets.*—Shape: Tubular, enlarged. Length: About 6 mm to 18 mm. Diameter: About 1 mm to 5 mm. Color: Immature: Towards the apex, close to 145A; mid-section, close to 150B; towards the base, close to 145D. Mature: Towards the apex, close to 4A; mid-section, close to 3C; towards the base, close to 145D.

*Involucral bracts.*—Length: About 5 mm to 10 mm. Width: About 3 mm to 6 mm. Shape: Ovate. Apex: Rounded. Base: Truncate. Margin: Entire. Texture, upper and lower surfaces: Smooth, glabrous. Number per inflorescence: About 15 to 20 arranged in two whorls. Color, upper surface: Close to 137B. Color, lower surface: Close to 137A.

*Peduncles.*—Length, fourth peduncle: About 9 cm. Length, seventh peduncle: About 12 cm. Diameter: About 2 mm to 3 mm. Angle: About 30° from vertical. Strength: Moderately strong to strong. Texture: Pubescent; longitudinally ridged. Color: Close to 137C.

*Reproductive organs.*—Androecium: Not observed. Gynoecium: Present on both ray and disc florets. Style length: About 5 mm. Stigma shape: Bi-parted. Stigma color: Close to 145A.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Mona Lisa Sunny' as illustrated and described.

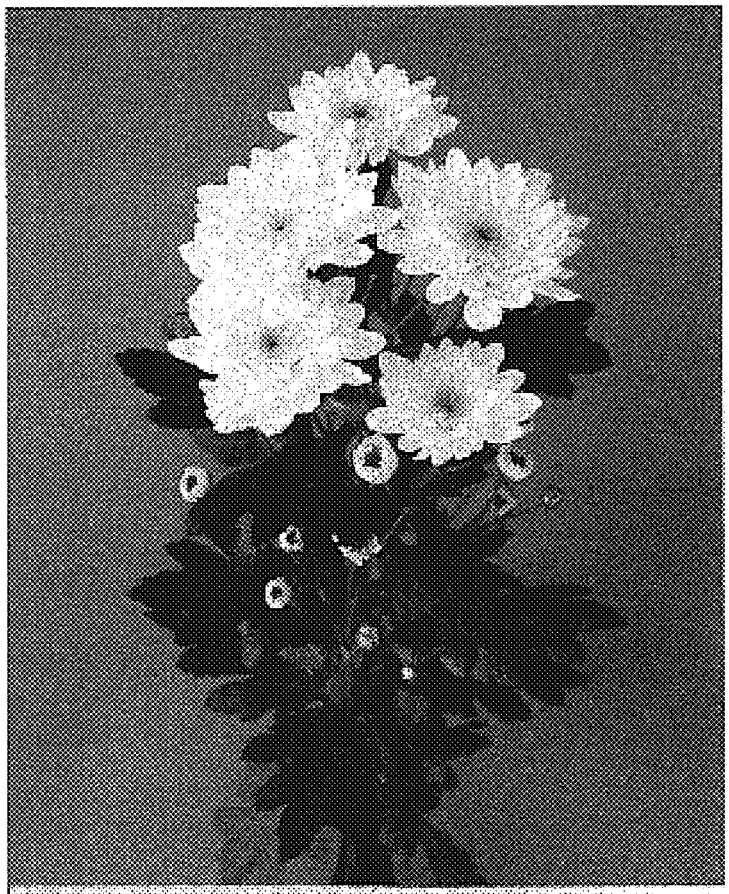
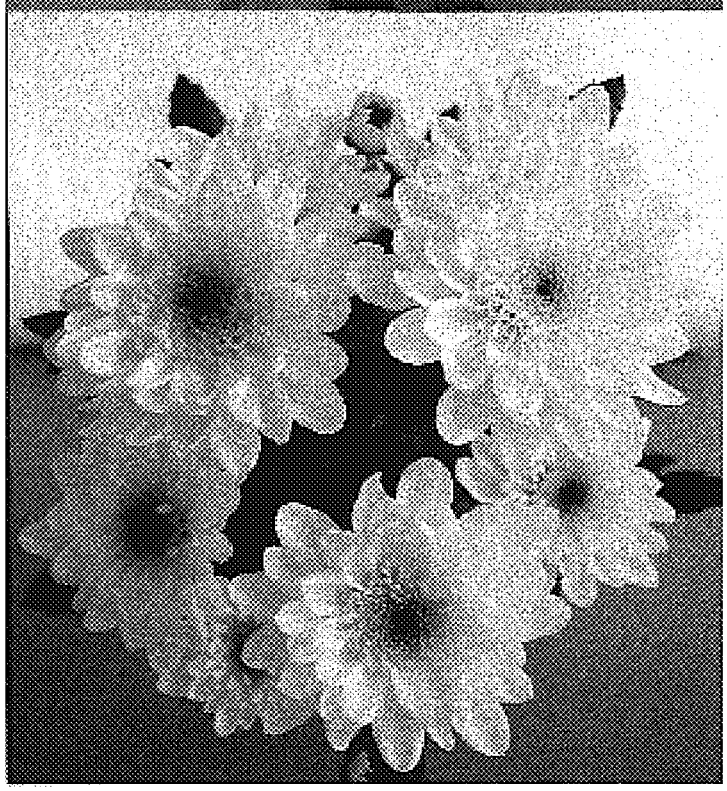

* * * * *